(12) United States Patent
Bae et al.

(10) Patent No.: US 8,071,382 B2
(45) Date of Patent: Dec. 6, 2011

(54) POROUS NANOFIBER MESH FOR THREE-DIMENSIONAL CELL CULTURE

(75) Inventors: Han-Ik Bae, Daegu (KR); In-Gyu Kang, Daegu (KR); Jun-Yong Mun, Daegu (KR); Young-Jin Kim, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 1097 days.

(21) Appl. No.: 11/722,239

(22) PCT Filed: Dec. 21, 2005

(86) PCT No.: PCT/KR2005/004433
§ 371 (c)(1),
(2), (4) Date: Jun. 20, 2007

(87) PCT Pub. No.: WO2006/068421
PCT Pub. Date: Jun. 29, 2006

(65) Prior Publication Data
US 2008/0009062 A1   Jan. 10, 2008

(30) Foreign Application Priority Data
Dec. 22, 2004  (KR) .................. 10-2004-0110269

(51) Int. Cl.
*C12N 5/07* (2010.01)
*C12N 11/08* (2006.01)
*C12Q 1/02* (2006.01)
*C12Q 1/04* (2006.01)

(52) U.S. Cl. ............ 435/395; 435/29; 435/34; 435/180
(58) Field of Classification Search .................. None
See application file for complete search history.

(56) References Cited

U.S. PATENT DOCUMENTS

| 6,838,089 | B1 * | 1/2005 | Carlsson et al. | 424/450 |
| 7,235,295 | B2 * | 6/2007 | Laurencin et al. | 428/364 |
| 7,309,345 | B2 * | 12/2007 | Wallace | 606/191 |
| 7,553,371 | B2 * | 6/2009 | Dubrow et al. | 117/90 |
| 7,704,740 | B2 * | 4/2010 | Schindler et al. | 435/398 |
| 2003/0050711 | A1 | 3/2003 | Laurencin et al. | |

FOREIGN PATENT DOCUMENTS
WO   WO 2005/047493 A2   5/2005

OTHER PUBLICATIONS

Mo et al., "Electrospun P(LLA-CL) nanofiber: a biomimetic extracellular matrix for smooth muscle cell and endothelial cell proliferation," *Biomaterials*, vol. 25, Issue 10, 2004 (pp. 1883-1890).
Yoshimoto et al., "A biodegradable nanofiber scaffold by electrospinning and its potential for bone tissue engineering," *Biomaterials*, vol. 24, No. 12, 2003 (pp. 2077-2082).
PCT International Search Report based on International Application No. PCT/KR2005/004433, date of mailing of the International Search Report Feb. 9, 2006 (2 pgs.).

* cited by examiner

*Primary Examiner* — David Naff
(74) *Attorney, Agent, or Firm* — Edwards Wildman Palmer LLP; Kongsik Kim

(57) ABSTRACT

Disclosed is a mesh for cell culture in which linear nanofiber is cross-linked to form a network, wherein the linear nanofiber is composed of polyhydroxyalkanoate; or polyhydroxyalkanoate, and collagen, gelatin or their mixture. The mesh for cell culture of the present invention can culture cell since the cell, more preferably the cancer cell is easily stuck to the mesh because of its structural characteristics and effect of the added collagen or gelatin, and also to smoothly supply nutrients, oxygen, etc. through connected pores. In particular, the mesh for cell culture of the present invention may be useful to culture the cancer cell.

8 Claims, 9 Drawing Sheets ably a mixture of polyhydroxyalkanoate and collagen or gelatin.

POROUS NANOFIBER MESH FOR THREE-DIMENSIONAL CELL CULTURE

TECHNICAL FIELD

The present invention relates to a nanofiber mesh for cell culture and a cell culture plate including the mesh.

BACKGROUND ART

Recently, many studies have been actively conducted in the cellular level owing to rapid development in the field of molecular biology, tissue engineering, genetic engineering, etc., and therefore there has been an increasing demand for cell culture. In the field of the tissue engineering, cell was, for example, cultured in vitro, and then the cultured cell was used for regenerating injured biological tissues of the human body such as muscular tissues, organs, etc., and developing artificial organs, etc. In the field of the medicine, the cell culture techniques have been used for developing bioactive compounds, medical supplies, etc. using proteins generated in the cultured cell. In these studies, the cell culture is necessarily required for increasing the cell counts, and there has been especially an increasing demand for effective cell culture in order to obtain antibodies, antigens, bioactive compounds, etc. from the cultured cell.

Such a cell culture technique may be also used for treating cancer in patients. Selecting a chemotherapy that has low side effects on patients and an excellent ability to suppress tumor cell growth is important to effectively treat cancer in the malignant tumor patients. It is very important to select anti-cancer drugs that can reduce the side effects and effectively suppress the tumor cell growth because anti-cancer drugs exhibits a different reaction level to the histopathologically identical category of the cancers according to the patients and damages hematopoietic cell of the bone marrow, hair-root cell, etc. which divide and grow rapidly among the normal cells. Therefore, there have been many attempts to culture the cancer cells as there has been an increasing demand for a susceptibility test of cancer cell on an anti-cancer drug in individual cancer patients, and also mechanisms of diseases (cancer cells) should be elucidated to effectively conduct a study to develop a novel drug such as anti-cancer drug, and sufficient amount of the cancer cell should be required for evaluating efficiency of the novel anti-cancer drug. There have been many studies on cancer cell culture, culture media, culture mesh, etc. for these purposes.

In the 1970's, the susceptibility test on the anti-cancer drug has been conducted with success of the in vitro culture of multiple myeloma using a double semisolid agar culture system by Hamburger and Salmon, but the culture system has problems that it has a low plating efficiency, a low cancer cell growth rate, etc.

Generally, if cell grows on a surface of a petri dish, then the cell does not grow any longer after it grows to a constant size, and therefore and it has a very low growth rate. In order to solve the problem, there has been a demand for a mesh for 3-D cell culture, more preferably a mesh for 3-D cell culture having a large specific surface area so that the cell can easily attach onto the mesh.

The conventional meshes for 3-D cell culture has disadvantages that its cell adhesion to the cell is not so excellent, as well as its specific surface area is not so large. Especially, a sponge-type mesh for cell culture, manufactured with collagen as a main component, has problems that the sponge-type mesh is deformed since it swells up in a culture medium, and the enzyme collagenase was used to remove collagen between the cultured cells to obtain the cell. Also, the meshes, generally used for the conventional 3-D cell cultures, have a problem that it is difficult to smoothly supply nutrients since its pores are not connected smoothly even if it is porous. Particularly due to the problem, it has problems that it is difficult to culture a cancer cell that grows very rapidly when compared to the general normal cells, and the cancer cell has a low growth rate.

DISCLOSURE OF INVENTION

Accordingly, the present invention is designed to solve the problems of the prior art, and therefore it is an object of the present invention to provide a mesh for cell culture capable of smoothly supplying nutrients, oxygen, etc to cell on the meshes since the cell is easily contacted with the mesh and its pores are systemically connected to each other.

In order to accomplish the above object, the present invention provides a porous mesh for cell culture capable of being used for a 3-D cell culture, wherein linear nanofiber composed of polyhydroxyalkanoate is cross-linked to form a network.

Preferably, the present invention provides a mesh for cell culture, wherein the linear nanofiber further includes collagen, gelatin, or their mixture in addition to said polyhydroxyalkanoate.

More preferably, the present invention provides a mesh for cell culture, wherein the linear nanofiber is composed of a mixture of polyhydroxyalkanoate (A) and collagen (B), the mixture having a weight ratio (B/A) of 2~10%.

More preferably, the present invention provides a mesh for cell culture, wherein the linear nanofiber is composed of a mixture of polyhydroxyalkanoate (A) and gelatin (B) having a weight ratio (B/A) of 10~100%.

More preferably, the present invention provides a mesh for cell culture, wherein the linear nanofiber has a diameter of 50 to 2,000 nm.

More preferably, the present invention provides a mesh for cell culture, wherein the polyhydroxyalkanoate composed of the mesh for cell culture is poly(3-hydroxybutyrate-co-3-hydroxyvalerate).

More preferably, the present invention provides a mesh for cell culture, wherein the mesh for cell culture is used for culturing cancer cell.

In addition, the present invention provides a polyethylene film for cell culture to which the mesh for cell culture is attached. More preferably, the present invention provides a cell culture plate including a plurality of the polyethylene film cut round to a suitable size for cell culture.

The present invention also provides a method for producing a porous mesh for cell culture capable of being used for a 3-D cell culture, including:

(S1) preparing a polyhydroxyalkanoate solution;
(S2) electrifying the solution with a positive charge; and
(S3) spraying the positively charged solution on a negatively charged material through a nozzle.

Preferably, the present invention provides a method for producing a mesh for cell culture, wherein the solution of the step (S1) further includes collagen, gelatin, or their mixture.

Hereinafter, a mesh for cell culture of the present invention and a producing method thereof will be described in detail.

The present invention provides a mesh for cell culture having a large specific surface area, wherein the mesh is a porous mesh capable of being used for a 3-D cell culture and linear nanofiber is cross-linked to form a network, the linear nanofiber composed of polyhydroxyalkanoate, more preferably a mixture of polyhydroxyalkanoate and at least on selected from the group consisting of collagen, gelatin or their mixture.

The mesh for cell culture of the present invention has a large specific surface area due to its structural characteristics to have a high aspect ratio (a ratio of length to diameter), that is, a large surface area that may be in contact with the cell therein, and therefore it is suitable for the cell culture, and the mesh of the present invention also has a structure in which its pores are smoothly connected to each other since the linear nanofiber is cross-linked in the mesh, and it is easy to supply nutrients, oxygen, etc., which are necessary for the cell culture through the pores, in all directions.

In order to conduct the 3-D cell culture, it is important to smoothly supplying the suitable nutrients and so on, and especially very important to smoothly supply the suitable nutrients, oxygen and so on, which are required for a rapid growth of cancer cell since the cancer cell grows rapidly unlike the general normal cells. In this aspect, the mesh of the present invention, in which the linear nanofiber is cross-linked to form a network, may be more useful for a cell culture, especially for a cancer cell culture since its pores are connected to each other so that the nutrients and so on can easily move through the pores.

As for the mesh for cell culture of the present invention, the linear nanofiber cross-linked to form a network more preferably has a diameter of 50 to 2,000 nm, collectively considering a specific surface area of the produced mesh, easy contact to cell, a size of the produced pores, etc.

The linear nanofiber constituting the mesh for cell culture of the present invention consists of a majority of polyhydroxyalkanoate. The polyhydroxyalkanoate is a carbon (energy) storage material accumulated within microorganisms as a hydrophilic material produced by the microorganisms. It has been known that such polyhydroxyalkanoate was generally biodegradable and non-toxic. Accordingly, because the mesh for cell culture of the present invention is biodegradable unlike the conventional meshes for cell culture composed only of collagen, it is further easy to separate the cell purely using the biodegradability of the mesh when only the cell should be separated after the cell culture.

The polyhydroxyalkanoate used for producing the mesh for cell culture of the present invention includes, but is not limited to, poly(3-hydroxypropionate), poly(3-hydroxybutyrate), poly(3-hydroxyvalerate(valerate)), poly(3-hydroxyhexanoate), poly(3-hydroxyoctanoate), poly(4-hydroxybutyrate), poly(5-hydroxyvalerate) and so on. Poly(3-hydroxybutyrate-co-3-hydroxyvalerate) (hereinafter, referred to as "PHBV") is more preferred, considering easy manufacturing, cell culture efficiency, etc. collectively.

The mesh for cell culture of the present invention is composed only of polyhydroxyalkanoate, or further includes collagen, gelatin, or their mixture. The mesh for cell culture of the present invention exhibits an enhanced hydrophilicity, and therefore an improved adhesion and histocompatibility of the cell since it further includes collagen, gelatin, or their mixture. Preferably, a weight ratio (B/A) of polyhydroxyalkanoate (A) and collagen (B) that constitute the mesh for cell culture preferably range from 2 to 10% if the collagen is further included in the mesh. The mesh shows a somewhat reduced adhesion if it is produced using polyhydroxyalkanoate with less than 2% by weight of collagen, while its manufacturing cost is increased and it is difficult to recover the cell after the cell culture due to extremely high adhesion if it is produced using polyhydroxyalkanoate with more than 10% by weight of collagen.

Preferably, a weight ratio (B/A) of polyhydroxyalkanoate (A) and gelatin (B) which constitute the mesh for cell culture preferably range from 10 to 100% if the gelatin is further included in the mesh owing to the same reason as described above in the collagen.

The present invention provides a method for producing a mesh for cell culture capable of being used for a 3-D cell culture, including:

(S1) preparing a polyhydroxyalkanoate solution, or (S1) preparing a mixture solution of polyhydroxyalkanoate, and collagen or gelatin;

(S2) electrifying the solution or the mixture solution with a positive charge; and (S3) spraying the positively charged solution or mixture solution on a negatively charged material through a nozzle.

FIG. 1 shows one preferred embodiment of a method for producing a mesh for cell culture of the present invention. As shown in FIG. 1, an apparatus for producing a mesh for cell culture of the present invention includes a high-pressure power supply unit; a syringe for spraying the aforementioned polyhydroxyalkanoate-including solution or mixture solution through a nozzle; a syringe pump for spraying a polymer mixture solution present in the syringe; and a rotary substance earthen at one end thereof and collecting nanofiber, sprayed and linearly formed, at a form of 3-dimensional mesh. A metal drum may be used as the rotary substance. A high-pressure electric field is connected to the syringe pump and the rotary substance in the high-pressure power supply unit, respectively. At this time, a positive voltage is applied in the syringe of the syringe pump, and a negative voltage is applied in the metal drum. The positively charged polymer mixture solution is elongated by the high-pressure electric field spanned from the nozzle of the syringe of the syringe pump to the metal drum, and therefore jet stream is generated in the solution elongated from a nozzle of the syringe to the earthen metal drum. Many nanofibers are divided in a spraying region, and then cross-linked on the rotating metal drum to obtain a mesh for cell culture forming a network.

The method for producing the mesh for cell culture of the present invention is very simple and easy, and it is easy to control a pore size of the mesh. Also, the mesh for cell culture of the present invention may be easily mass-produced, and also easily produced by adding useful inorganic materials for the cell culture, as well as organic polymers in the form of a solution or molten solution.

The present invention also provides a polyethylene film to which the mesh for cell culture is attached so that the mesh can be substantially easily used. More preferably, the present invention also provides a cell culture plate obtained by cutting the plate-shaped polyethylene film, to which the mesh for cell culture is attached, to a suitable size and shape for the cell culture using a press, etc., and then aggregating a large number of the cut polyethylene film densely (see FIG. 16).

The mesh for cell culture according to the present invention is characterized in that linear nanofiber is cross-linked to form a network, wherein the linear nanofiber is composed of polyhydroxyalkanoate; or polyhydroxyalkanoate, and collagen, gelatin or their mixture, and therefore the mesh for cell culture of the present invention may be useful to culture cell since the cell, more preferably the cancer cell is easily stuck to the mesh because of its structural characteristics and effect of the added collagen or gelatin, and also to smoothly supply nutrients, oxygen, etc. through connected pores.

BRIEF DESCRIPTION OF THE DRAWINGS

These and other features, aspects, and advantages of preferred embodiments of the present invention will be more fully described in the following detailed description, taken accompanying drawings. In the drawings.

BEST MODES FOR CARRYING OUT THE INVENTION

Hereinafter, preferred examples of the present invention will be described in detail referring to the accompanying drawings. However, it should be understood that the detailed description proposed herein is just a preferable example for the purpose of illustrations only, not intended to limit the scope of the invention, so it should be understood that other equivalents and modifications could be made thereto without departing from the spirit and scope of the invention.

<Preparation of Mesh for Cell Culture According to the Present Invention and Plate Including the Same>

Example 1-1

Preparation of Mesh for Cell Culture Composed Only of PHBV

Figure 1:
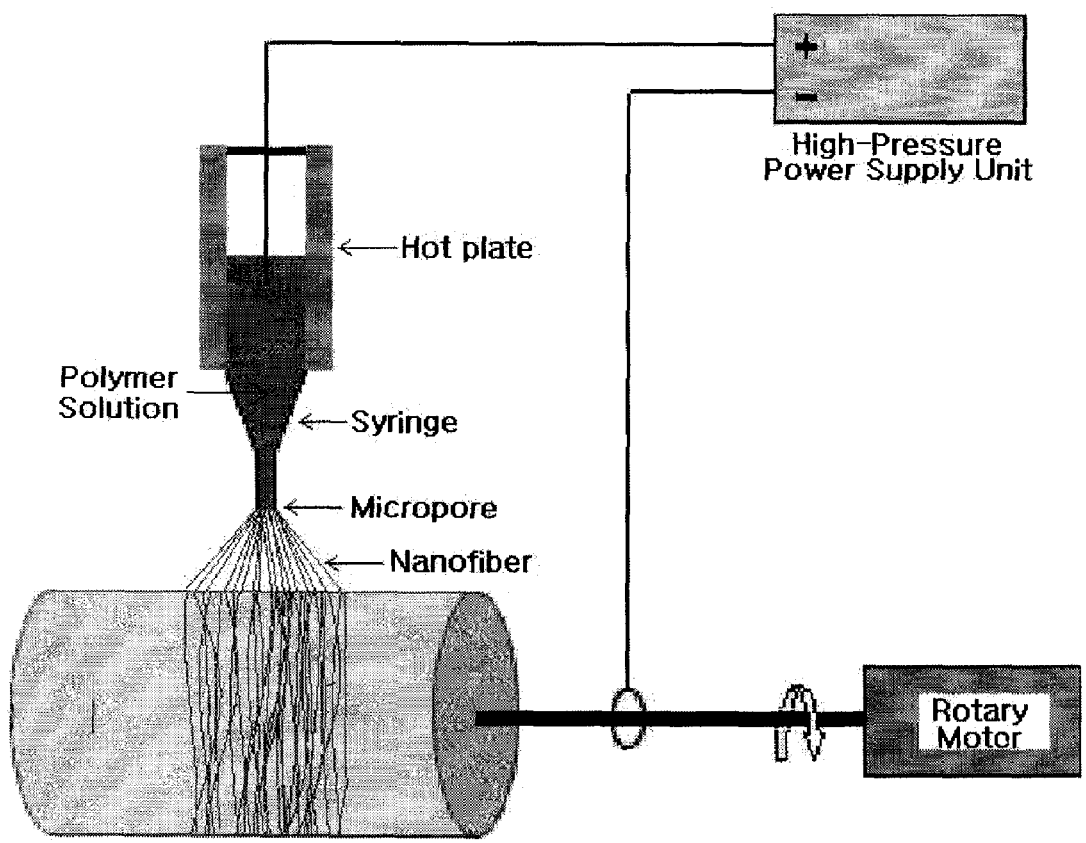
FIG. 1 is a schematic view showing an apparatus for producing a mesh for cell culture of the present invention.

Poly(3-hydroxybutyrate-co-3-hydroxyvalerate) was dissolved in an equivalent amount of a solvent hexafluoro-2-propanol to prepare a polymer solution. A mesh for cell culture was then produced using a producing apparatus of the mesh for cell culture as shown in FIG. 1. A distance between a syringe nozzle and a metal drum was set to approximately 12 cm upon its production, and 10 KV of voltage was applied, and it was maintained under the following condition: a humidity of less than 20% and a temperature of at least 40° C. The mesh was vacuum-dried for 24 hours after its production.

Example 1-2

Preparation of Mesh for Cell Culture Composed of PHBV and Collagen

Figure 2:
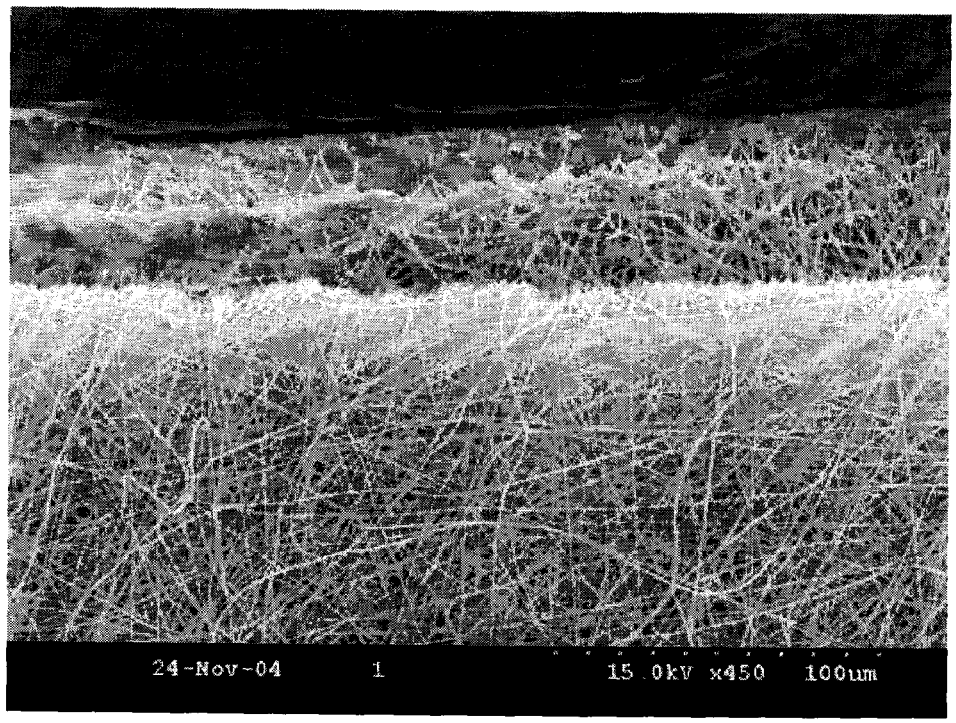
FIG. 2 is an SEM photograph showing the nanofiber mesh for cell culture produced with polyhydroxyalkanoate and collagen according to one embodiment of the present invention.
Figure 3:
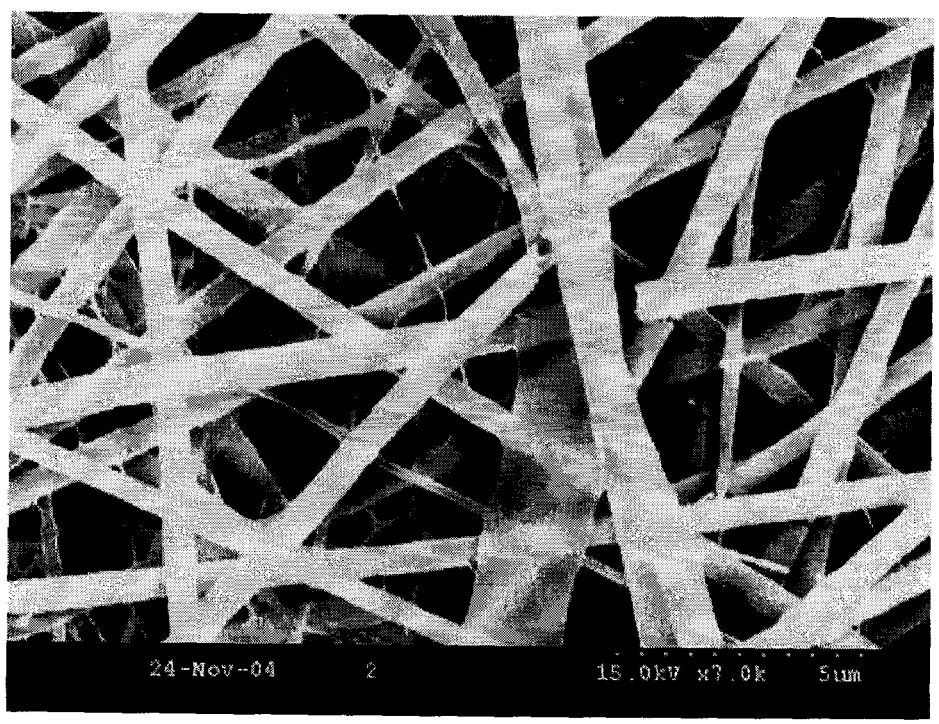
FIG. 3 is an SEM photograph showing a partially magnified section of FIG. 2. It was observed that linear or plate-shaped fine collagen is present between nanofibers composed of polyhydroxyalkanoate.

A 6 equivalent amount of collagen was mixed with poly(3-hydroxybutyrate-co-3-hydroxyvalerate) on the basis of the total amount of PHBV, and then dissolved in an equivalent amount of a solvent hexafluoro-2-propanol to prepare a polymer mixture solution. A mesh for cell culture was then produced in the same manner as in Example 1-1. SEM photographs showing the produced mesh are shown in FIGS. 2 and 3.

Example 1-3

Preparation of Mesh for Cell Culture Composed of PHBV and Gelatin

Figure 4:
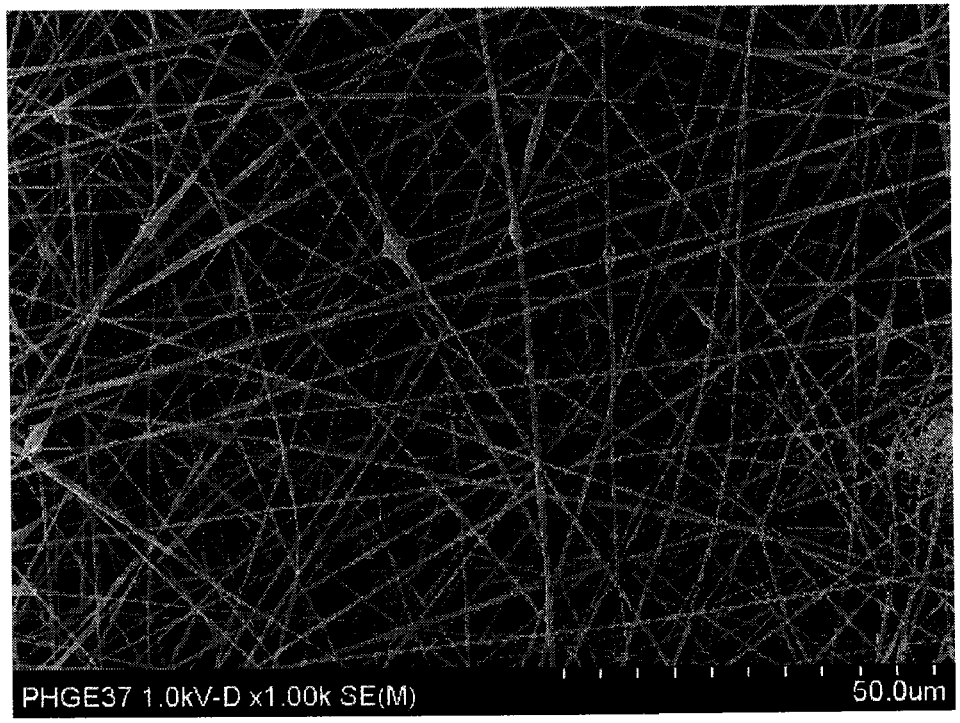
FIG. 4 is an SEM photograph (1,000×) showing the nanofiber mesh for cell culture produced with polyhydroxyalkanoate and gelatin according to one embodiment of the present invention.
Figure 5:
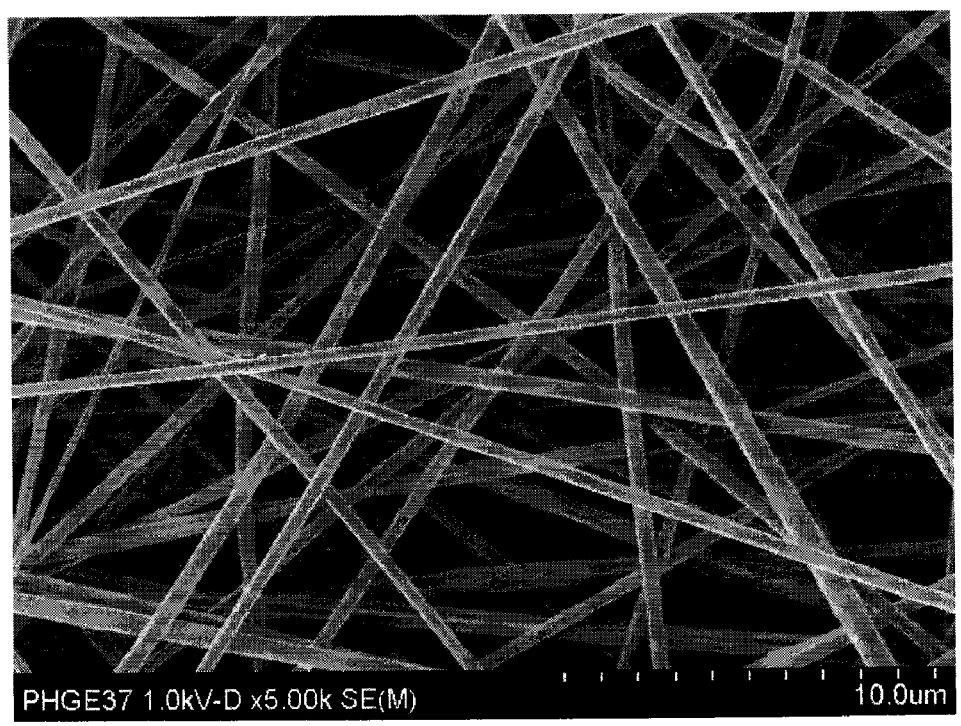
FIG. 5 is an SEM photograph (5,000×) showing the nanofiber mesh for cell culture produced with polyhydroxyalkanoate and gelatin according to one embodiment of the present invention.

Poly(3-hydroxybutyrate-co-3-hydroxyvalerate) and gelatin were mixed at a weight ratio of 70:30%, and then dissolved in an equivalent amount of a solvent hexafluoro-2-propanol to prepare a polymer mixture solution. A mesh for cell culture was then produced in the same manner as in Example 1-1. SEM photographs showing the produced mesh are shown in FIGS. 4 and 5.

Example 1-4

Preparation of Cancer Cell Culture Plate

Figure 16:
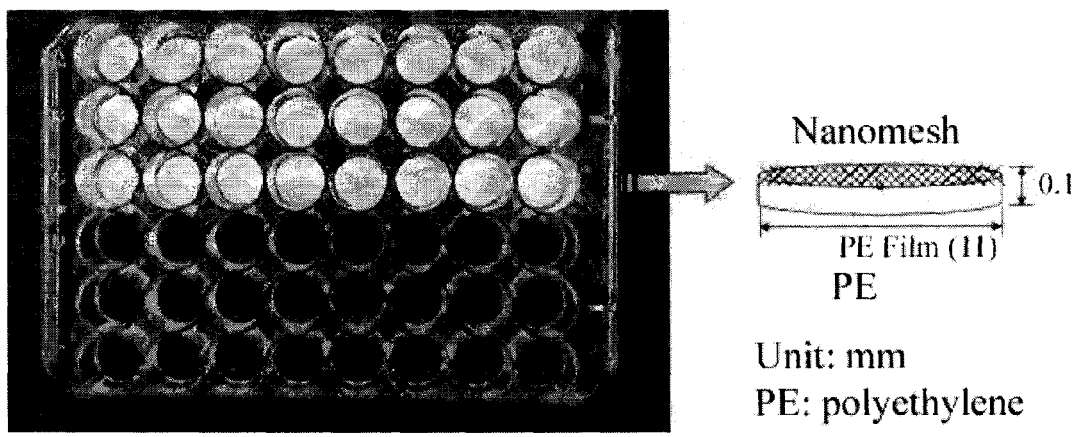
FIG. 16 is a photograph showing circular polyethylene films to which the nanofiber mesh for cell culture of the present invention is attached, and a cell culture plate in which a large number of the polyethylene films are densely aggregated.

The meshes produced in Examples 1-1 to 1-3 were sterilized in order of ethanol (75%, 50%, 25%) from high concentration to low concentration, washed with PBS, and dried. Then, the washed and dried meshes for cell culture were attached to one surface of a polyethylene film having a half size of A4 paper (210×297 mm), and then cut with a press to be a circular form having a diameter of 11 mm. The cut polyethylene films were then put into a plate having a plurality of circular grooves prepared previously, as shown in FIG. 16.

<Evaluation of Cell Culture>

Example 2-1

Cell Culture Test Using Primarily Cultured Ovarian Cancer Cell

A cell solution was prepared by counting the primarily cultured ovarian cancer cell to the suitable cell number ($3\times10^4$-$5\times10^4$), and 700 µl of the primarily cultured ovarian cancer cell solution prepared above was loaded into the plate of Example 1-2, and cultured at 37° C. for 3 hours under a 5% $CO_2$ atmosphere. A culture solution was removed from the well, and then the cell was slightly washed with a phosphate-buffered saline and fixed with 2.5% glutaraldehyde for 30 minutes. The cell was slightly washed with tridistilled water, and then dehydrated while being dried out in a clean bench in order of ethanol (25%, 50%, 75%, 100%) from low concentration to high concentration. The mesh was then dried for 16 hours after treatment with 100% ethanol. The dried mesh was then cut to a size of approximately 0.5 cm, and then its SEM (Scanning Electron Microscope) photograph was taken. The mesh was observed at an accelerating voltage of 20 kV using a Hitachi S4,300 scanning electron microscope (the company Hitachi, Japan), its sections of interest were selected and taken by the scanning electron microscope to obtain images of the mesh. The results are shown in FIGS. 6 and 7.

Figure 6:
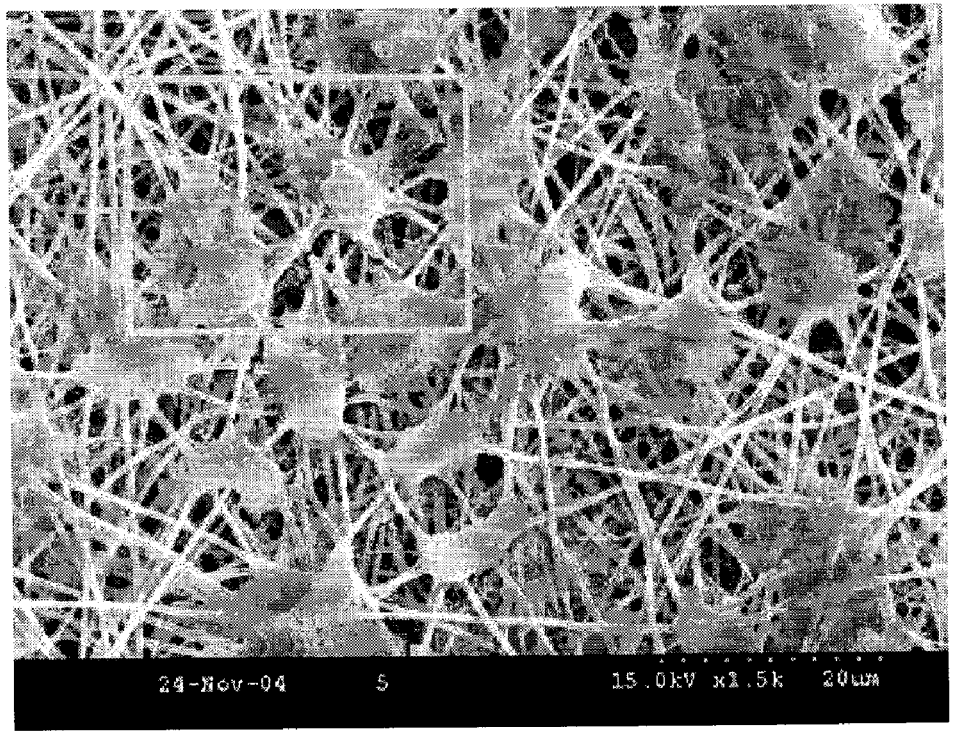
FIG. 6 is an SEM photograph showing ovarian cancer cell which is obtained from tissue of an ovarian cancer patient, and then primarily cultured in the nanofiber mesh for cell culture according to one embodiment of the present invention.
Figure 7:
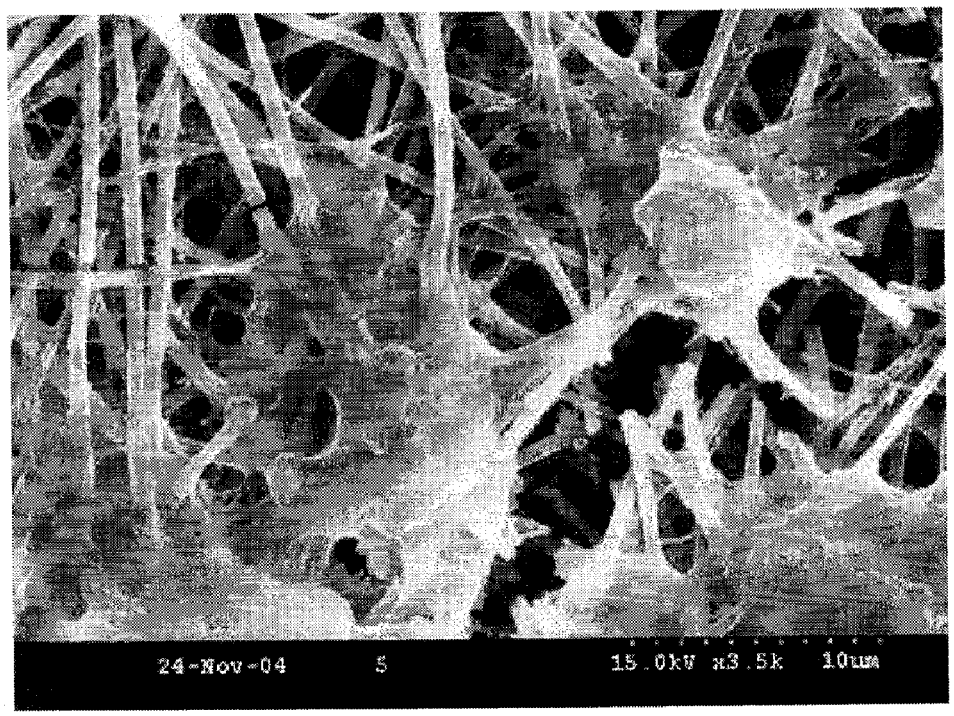
FIG. 7 is an SEM photograph showing a partially magnified section of FIG. 6.

FIGS. 6 and 7 show photographs taken by the scanning electron microscope 3 hours after the primarily cultured ovarian cancer cell was primarily spread over the mesh of the present invention. It was seen that the ovarian cancer cell was closely attached to the mesh with extended legs during a treatment procedure of the scanning electron microscope including fixation, dehydration, washing, etc.

Example 2-2

Cell Culture Test Using HCT116 Colon Cancer Cell

A cell culture test was repeated in the same manner as in Example 2-1, except that the HCT116 colon cancer cell (KCLB No. 10247, Korean Cell Line Bank) was used instead of the ovarian cancer cell, and the mesh of Example 1-1 was used instead of the mesh of Example 1-2 and cultured for 1 day. The results are shown in FIGS. 8 and 9.

Figure 8:
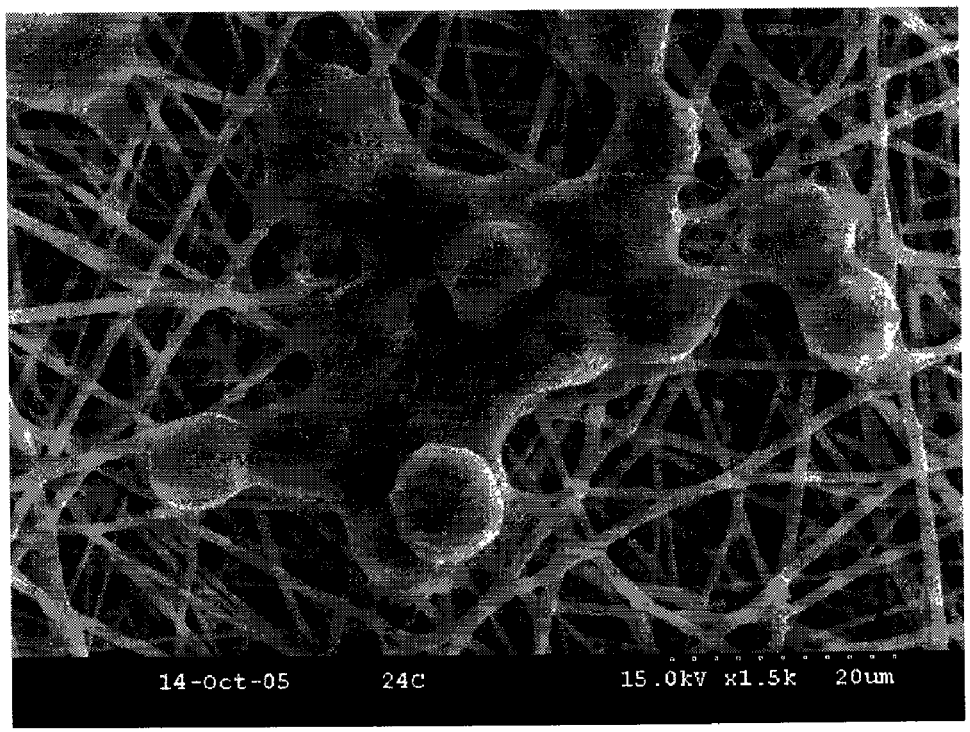
FIG. 8 is a scanning electron microscope (SEM) photograph of cancer cell, taken at magnification of 1,000 times, showing that a HCT116 colon cancer cell is cultured for 1 week in the nanofiber mesh whose nanofiber is produced only with polyhydroxyalkanoate.
Figure 9:
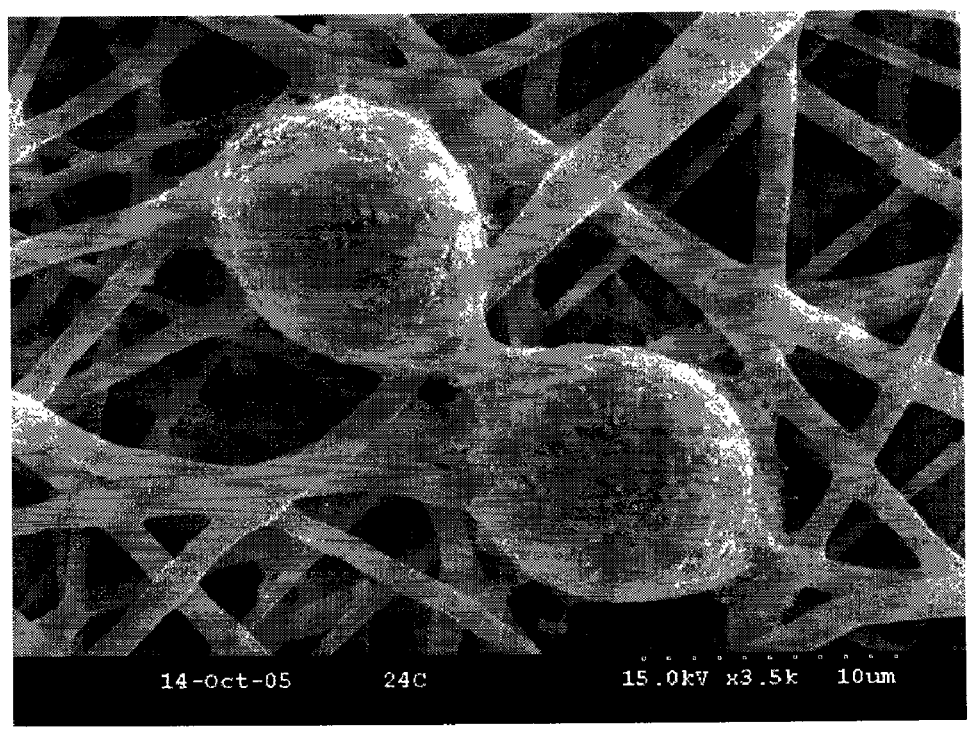
FIG. 9 is a scanning electron microscope (SEM) photograph of cancer cell, taken at magnification of 5,000 times, showing that a HCT116 colon cancer cell is cultured for 1 week in the nanofiber mesh whose nanofiber is produced only with polyhydroxyalkanoate.

FIGS. 8 and 9 show photographs taken by the scanning electron microscope 3 hours after the primarily cultured colon cancer cell was primarily spread over the mesh of the present invention. It was seen that the colon cancer cell was closely attached to the mesh with extended legs during a treatment procedure of the scanning electron microscope including fixation, dehydration, washing, etc. FIGS. 8 and 9 are scanning electron microscope (SEM) photographs of the cancer cell, taken at magnification of 1,000 and 5,000 times respectively, showing that a HCT116 colon cancer cell line was cultured for 1 week in the mesh produced only with PHBV. If the mesh was produced only with PHBV, then foreign substances were not observed around the cell, and the cell grew into a cluster and overlapped to remain engrafted well, as shown in FIG. 8. Also, the colon cancer cell was strongly attached to the nanofiber mesh while maintaining cytoplasmic processes without any change of the cell, as shown in FIG. 9.

Example 2-3

Cell Culture Test Using Normal Chondrocyte and Normal Fibroblast of Rat

Chondrocyte was separated from the knee joint of a white rat (Splague-Dawley rat) immediately after the white rat was killed, and a cell culture test of the normal chondrocyte was conducted with the mash composed only of PHBV prepared in Example 1-1 in the similar manner to Example 2-2. The result is shown in FIG. 10.

Also, a white rat (Splague-Dawley rat) was anesthetized, and then its abdominal wall was incised to remove fibroblast that produces hypodermic collagen fiber, and a cell culture test of the normal chondrocyte was conducted with the mash composed of PHBV and the collagen prepared in Example 1-2 in the similar manner to Example 2-2. The result is shown in FIG. 11.

Figure 10:
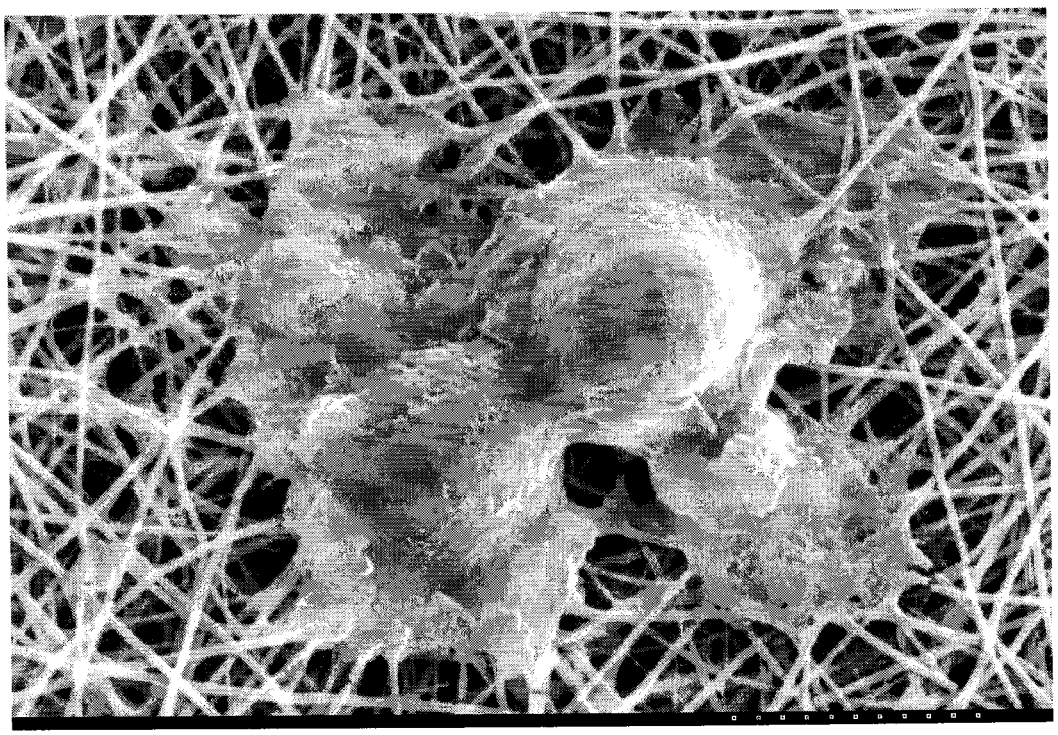
FIG. 10 is a scanning electron microscope (SEM) photograph showing that normal chondrocyte is cultured in the nanofiber mesh for cell culture produced with polyhydroxyalkanoate and collagen according to one embodiment of the present invention.

FIG. 10 shows a photograph taken by the scanning electron microscope 2 hours after the chondrocyte was primarily spread over the mesh of the present invention. It was seen that the chondrocyte was strongly attached to the mesh of the present invention.

Figure 11:
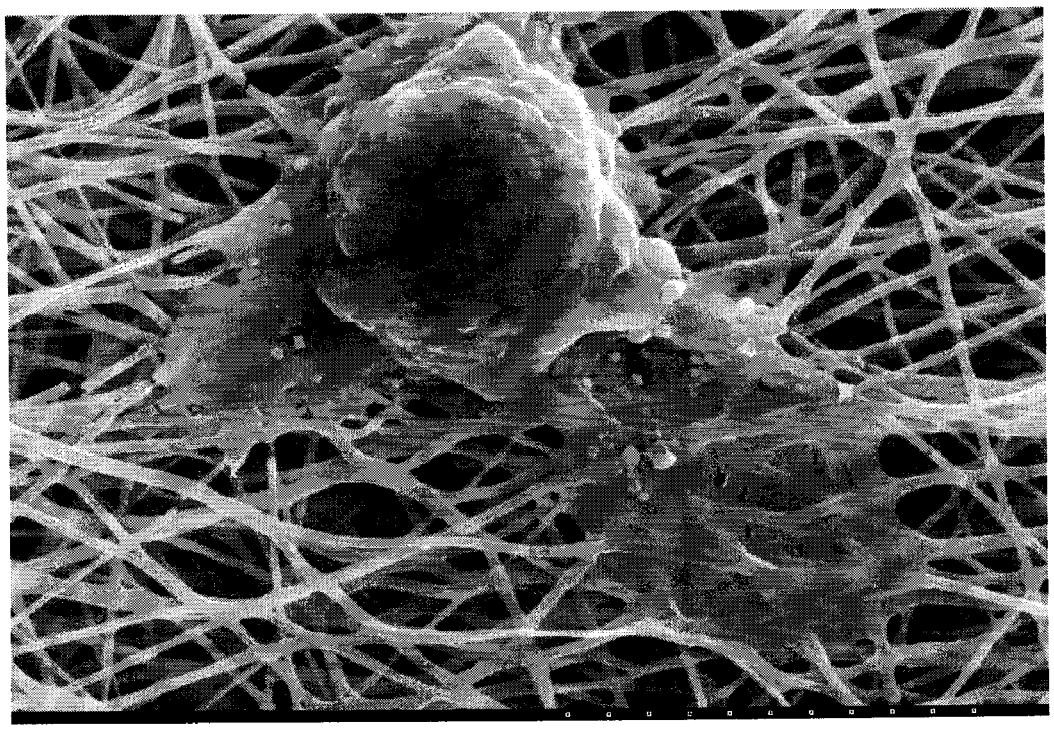
FIG. 11 is a scanning electron microscope (SEM) photograph showing that normal fibroblast of a white rat is cultured in the nanofiber mesh for cell culture composed of polyhydroxyalkanoate according to one embodiment of the present invention.

FIG. 11 shows a photograph taken by the scanning electron microscope 2 hours after the primarily cultured fibroblast of the white rat was primarily spread over the mesh of the present invention. It was seen that the fibroblast was strongly attached to the mesh of the present invention while forming cytoplasmic processes well.

Example 2-4

Cell Culture Test Using HCT116 Colon Cancer Cell

A cell culture test was repeated in the same manner as in Example 2-2, except that an HCT116 colon cancer cell (KCLB No. 10247, Korean Cell Line Bank) and the mesh prepared in Example 1-2 were used herein. The result is shown in FIG. 14.

Figure 14:
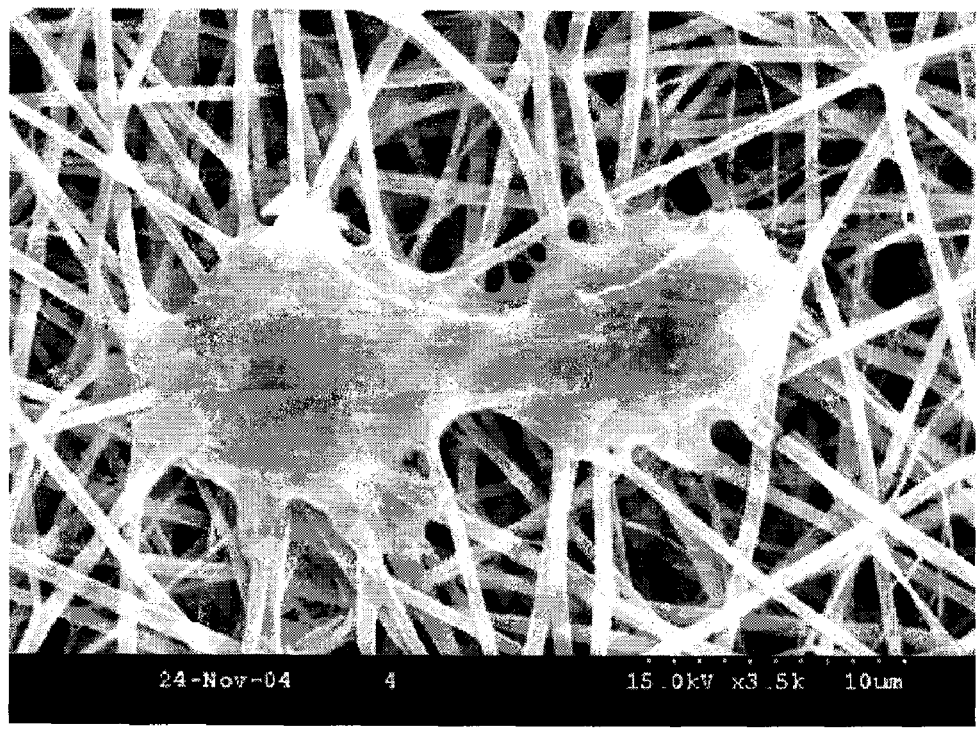
FIG. 14 is an SEM photograph showing that HCT116 colon cancer cell is cultured in the nanofiber mesh for cell culture of the present invention.

FIG. 14 shows a photograph taken by the scanning electron microscope 3 hours after the primarily cultured colon cancer cell was primarily spread over the mesh of the present invention. It was seen that the HCT116 colon cancer cell was strongly attached to the nanofiber in the mesh of the present invention.

Comparative Example 1-1

Cell Culture Test Using Primarily Cultured Ovarian Cancer Cell

A cell culture test was repeated in the same manner as in Example 2-1, except that a petri dish coated with collagen was used instead of the mesh for cancer cell culture of the present invention. The results are shown in FIGS. 12 and 13.

Figure 12:
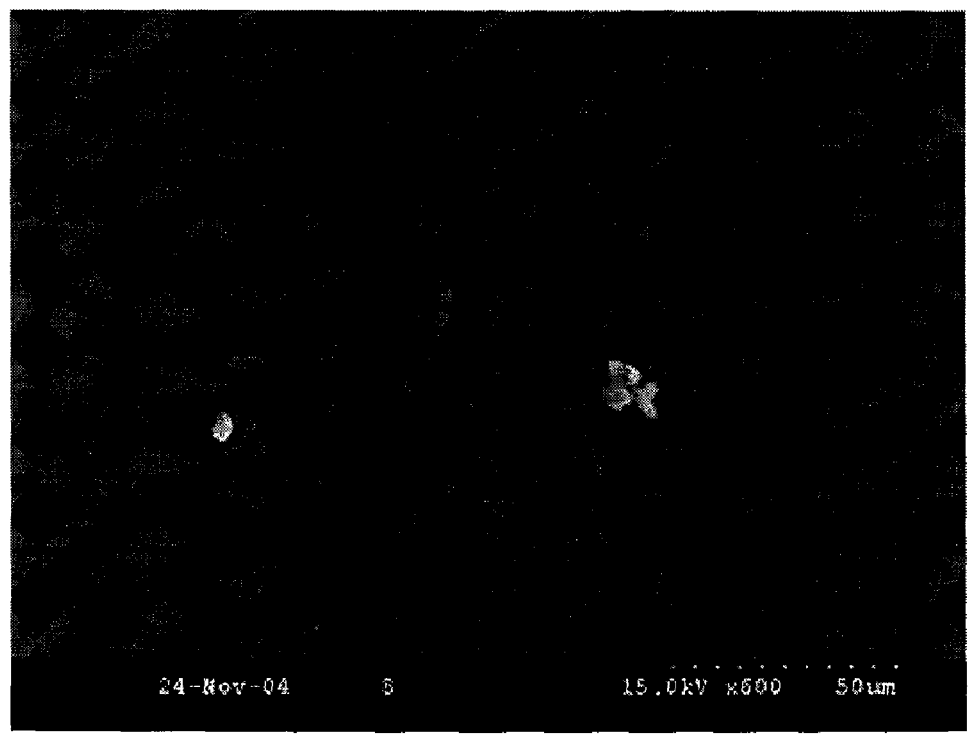
FIG. 12 is an SEM photograph showing an ovarian cancer cell primarily cultured on a petri dish coated with collagen.
Figure 13:
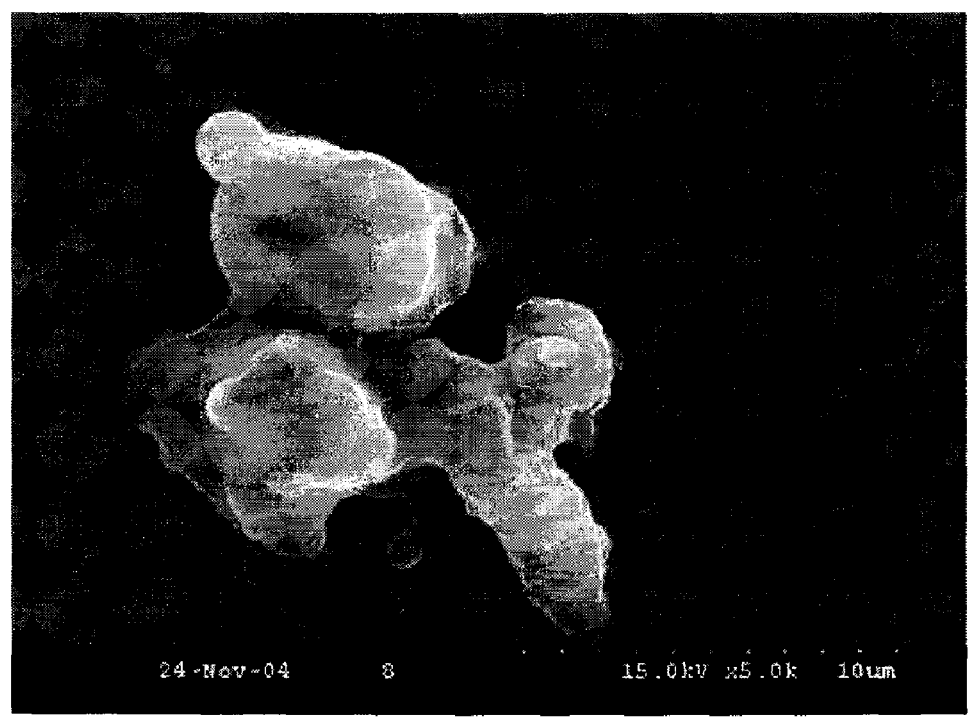
FIG. 13 is an SEM photograph showing a partially magnified section of FIG. 12.

FIGS. 12 and 13 show photographs taken by the scanning electron microscope 3 hours after the primarily cultured ovarian cancer cell was primarily spread over the petri dish coated with collagen. It was seen that four cells grew while being attached to each other. The number of the ovarian cancer cell was smaller than that of the cell cultured in the mesh of the present invention since the ovarian cancer cell was detached during a treatment procedure of the scanning electron microscope including fixation, dehydration, washing, etc.

Comparative Example 1-2

Cell Culture Test Using HCT116 Colon Cancer Cell

A cell culture test was repeated in the same manner as in Example 2-4, except that HCT116 colon cancer cell was used instead of the ovarian cancer cell. The result was shown in FIG. 15.

Figure 15:
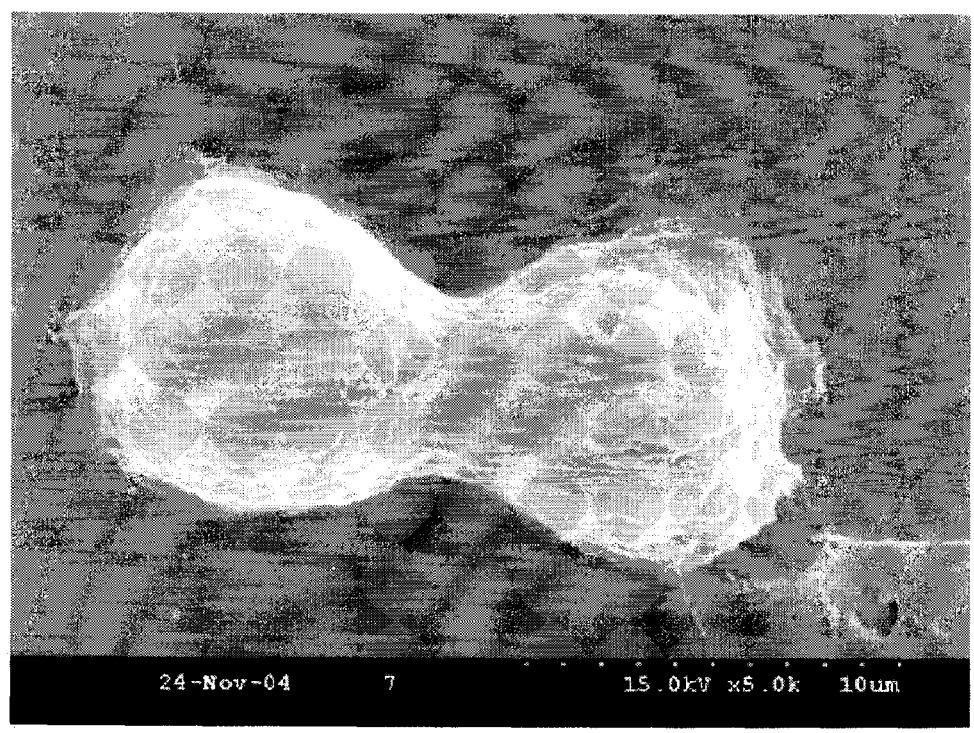
FIG. 15 is an SEM photograph showing that HCT116 colon cancer cell is cultured on a petri dish coated with collagen.

As shown in FIG. 15, it was revealed that the HCT colon cancer cell cultured on the petri dish coated with collagen was poorly engrafted unlike the result of FIG. 14.

What is claimed is:

1. A porous mesh for cell culture capable of being used for a three-dimensional cell culture, said mesh comprising nanofibers cross-linked to each other to form a network, wherein the nanofibers are formed of mixture of poly(3-hydroxybutyrate-co-3-hydroxyvalerate) and collagen, and
   wherein the mixture comprises a weight ratio of collagen to poly(3-hydroxybutyrate-co-3-hydroxyvalerate) of 2-10%.

2. A porous mesh for cell culture capable of being used for a three-dimensional cell culture, said mesh comprising nanofibers cross-linked to each other to form a network, wherein the nanofibers are formed of a mixture of poly(3-hydroxybutyrate-co-3-hydroxyvalerate) and gelatin, and
   wherein the mixture comprises a weight ratio of gelatin to poly(3-hydroxybutyrate-co-3-hydroxyvalerate) of 10-100%.

3. The mesh for cell culture according to claim 1, wherein each of the nanofibers has a diameter in the range of 50 to 2,000 nm.

4. The mesh for cell culture according to claim 2, wherein each of the nanofibers has a diameter in the range of 50 to 2,000 nm.

5. A cell culture plate comprising a mesh of claim 1 and a polyethylene film attached to the mesh.

6. A cell culture plate comprising a mesh of claim 2 and a polyethylene film attached to the mesh.

7. A cell culture plate comprising a mesh of claim 3 and a polyethylene film attached to the mesh.

8. A cell culture plate comprising a mesh of claim 4 and a polyethylene film attached to the mesh.

* * * * *